(12) United States Patent
Kuwabara et al.

(10) Patent No.: US 7,691,625 B2
(45) Date of Patent: Apr. 6, 2010

(54) CELL CULTURAL VESSEL, PRODUCTION PROCESS THEREOF AND CULTURED CELL

(75) Inventors: Kosuke Kuwabara, Hitachi (JP); Akihiro Miyauchi, Hitachi (JP); Norihito Kuno, Tsurugashima (JP)

(73) Assignee: Hitachi, Ltd. (JP)

( * ) Notice: Subject to any disclaimer, the term of this patent is extended or adjusted under 35 U.S.C. 154(b) by 985 days.

(21) Appl. No.: 11/441,235

(22) Filed: May 26, 2006

(65) Prior Publication Data

US 2006/0281172 A1 Dec. 14, 2006

(30) Foreign Application Priority Data

May 30, 2005 (JP) .............................. 2005-156551

(51) Int. Cl.
- *C12M 1/14* (2006.01)
- *C12M 3/04* (2006.01)
- *C12M 3/00* (2006.01)
- *C12M 1/00* (2006.01)

(52) U.S. Cl. .............. 435/305.1; 435/283.1; 435/284.1; 435/285.1; 435/285.2; 435/285.3; 435/286.1; 435/286.7; 435/287.1; 435/287.9; 435/288.1; 435/288.7; 435/289.1; 435/290.1; 435/290.2; 435/290.3; 435/290.4; 435/291.8; 435/291.1; 435/293.1; 435/293.2; 435/294.1; 435/295.1; 435/295.3; 435/296.1; 435/297.1; 435/297.5; 435/298.1; 435/299.1; 435/299.2; 435/300.1; 435/301.1; 435/302.1; 435/303.1; 435/303.2; 435/303.3; 435/304.1; 435/304.3; 435/305.4; 435/306.1; 435/307.1; 435/308.1; 435/309.1; 435/309.4

(58) Field of Classification Search .... 435/283.1–309.4
See application file for complete search history.

(56) References Cited

U.S. PATENT DOCUMENTS

| | | | | |
|---|---|---|---|---|
| 4,761,378 A | * | 8/1988 | Godsey | 435/288.4 |
| 4,975,377 A | * | 12/1990 | Key | 435/297.5 |
| 5,084,393 A | * | 1/1992 | Rogalsky | 435/299.2 |
| 5,264,344 A | * | 11/1993 | Sneath | 435/7.32 |
| 6,852,525 B1 | * | 2/2005 | Cantor | 435/288.3 |
| 7,195,872 B2 | * | 3/2007 | Agrawal et al. | 435/6 |

FOREIGN PATENT DOCUMENTS

| | | |
|---|---|---|
| JP | 2002-142751 | 5/2002 |
| JP | 2004-170935 | 6/2004 |

* cited by examiner

*Primary Examiner*—Walter D Griffin
*Assistant Examiner*—Lydia Edwards
(74) *Attorney, Agent, or Firm*—Antonelli, Terry, Stout & Kraus, LLP.

(57) ABSTRACT

An object of the present invention is to provide a cell culture vessel which is simple in structure and easy to handle, and is capable of preventing damage to the cells when separated, promoting transport of nutrients and excretion of effete matter, and elevating the culturing efficiency improving effect by the structural features. In order to attain the above object, there is provided a cell culture vessel including a culture section provided with a plurality of projections having an equivalent diameter smaller than the cells to be cultured and the culture section side walls enclosing the culture section, wherein the distance between an arbitrary position on the culture section/side wall boundary line and the nearest projection is smaller than the diameter of the cells to be cultured. The effect of the projections in the vessel given to the cultured cells is enhanced.

20 Claims, 9 Drawing Sheets

103

CELL CULTURAL VESSEL, PRODUCTION PROCESS THEREOF AND CULTURED CELL

BACKGROUND OF THE INVENTION

The present invention relates to a cell culture vessel having excellent cell separatability, a production process thereof, and cells cultured in such a culture vessel.

The recent years have seen remarkable progress of the techniques for culture of cells used for medical purposes, and the cultured cells are actually used for grafting of the skin. There has also been seen progress in cell culturing techniques to be applied to autologous transplantation and heterologous transplantation, which application is not limited to grafting of simple tissues such as skin but extends to transplantation of more complex organs such as cornea, tooth, bone and viscera.

Various vessels such as glass or resin-made Petri dish are used for culture of cells. For instance, the Petri dishes for cell culture made by the following methods have been disclosed. In one method, a collagen solution of a specified concentration is pipetted to a culture vessel for coating such as to form a uniform surface and then dried for 15 minutes to 72 hours. In another method, a collagen solution of a specified concentration is coated on a flexible culture base material such as silicone membrane and polymerized in a 15-42° C. incubator for 20-120 minutes, then the flexible culture substrate is left under UV lamp irradiation for 15 minutes to 72 hours, and after collagen has been dried away, the substrate is again wetted with a phosphate butter solution, then extended 10-40% and fixed (see JP-A-2002-142751, e.g., Example A).

According to the first method, although it is possible to culture a cell on collagen having affinity for the cell, difficulties are involved in separating the cell because of strong adhesion between the cell and the culture vessel. If the cell is separated by mechanical means, physical damage may be given to the cell, and when a chemical treatment with an enzyme such as trypsin is applied on the cell, the membrane protein in the cell surface may be destroyed to reduce the cell fixing rate to the tissue after grafting.

The present inventors previously disclosed, in the below-mentioned patent, a cell culture vessel free of the above problem. In this patent, the cell is cultured on a functional substrate provided with organic polymer-made columnar microprojections capable of shape controlling, whereby the culture solution can be readily placed below the cell and also cell separatability is improved (see JP-A-2004-170935, e.g., Example 5).

According to the second method mentioned above, the problem relating to separation of the cell is solved by lowering adhesion between the cell and the culture vessel by reducing the area of the culture vessel surface where the cell is brought into contact. This method, however, had the problem that the cell would be adsorbed even to the sheet end or the portion of the dish bottom where the functional substrate is absent, causing a drop of cell culturing efficiency. Further, in case the cells cultured on the microprojections exhibit the properties different from those shown when the cells are cultured in an ordinary culture vessel, the cells cultured on the microprojections may be mixed with the cells cultured on a flat portion having no microprojections.

It is therefore an object of the present invention to provide a cell culture vessel which is simple in structure and easy to handle, and is capable of preventing damage to the cells when separated, promoting transport of nutrients and excretion of effete matter, and elevating the culturing efficiency improving effect by the structural features.

SUMMARY OF THE INVENTION

In order to solve the above problems, the present invention provides, in a first embodiment thereof, a cell culture vessel comprising a culture section provided with a plurality of projections having an equivalent diameter smaller than the cells to be cultured and the culture section side walls enclosing said culture section, wherein the space between any portion of said side walls and the projection located nearest thereto on the culture section is smaller than the diameter of the cells to be cultured. In this cell culture vessel, there is eliminated any projection-absent portion near the edge of the culture section so as to maximize the effect of the projections on the cells. The term "equivalent diameter" is used in the present invention to accommodate all possible sectional shapes of the projections which are not necessarily circular but may be elliptical, polygonal, asymmetric or other shapes. In the present invention, the equivalent diameter is the diameter of a section at the bottom of the projections.

In some cell lines with strong adhesiveness to the vessel, adsorption of the cells to the culture section side walls is unnegligible, and there are the cell lines in which it is undesirable that the cells cultured on the side wall be mixed with those on the culture section. For such lines, it is the best to provide the similar projections on the culture section side walls, too, but in case it is difficult to provide such projections, the culture section side walls may be made non-adhesive to the cells by adopting a specific structure or using a specific material for the side walls. By forming a buffer section, positioned at a lower level than the culture section, between the culture section having the microprojections and the side walls, it is possible to prevent the cells adsorbed to the side walls from moving to transfer to the culture section having the projections. In this case, too, it is possible to maximize the effect of the microprojections on the cells by setting the distance between the microprojection closest to the buffer section and the edge of the culture section to be smaller than the diameter of the cells to be cultured.

In order to allow the culture solution to pervade over the culture section, the surface of the culture section of the cell culture vessel may be treated to be hydrophilic to accelerate the flow of the culture solution. However, for certain kinds of cells to be cultured, it may be required to treat the vessel surface to be hydrophobic or to coat the vessel surface with a metal or a protein. In the present invention, therefore, a hydrophobicity treatment or other treatments such as metal or protein coating necessary for the cell culture may be applied only on the top end portions of the microprojections where the cells are brought into contact in the cell culture vessel.

In case where it is desired to afford specific properties, such as orientation, to the cells to be cultured, a specific treatment such as hydrophobicity treatment may be applied partially on the bottom surface of the cell culture vessel according to the properties to be afforded to the cells. In the present invention, a treatment necessary for cell culture, such as hydrophobicity treatment or metal or protein coating, can be applied selectively to the top ends of the microprojections on the surface of the cell culture vessel.

Applying the present invention has the effects of preventing damage to the cells when separated, promoting transport of nutrients and excretion of effete matter and enhancing the cultivation effect by the projections. It is also possible to derive the effect of preventing the cells cultured at the no-projection area from being mixed with the cells on the projections.

Other objects, features and advantages of the invention will become apparent from the following description of the embodiments of the invention taken in conjunction with the accompanying drawings.

DESCRIPTION OF REFERENCE NUMERALS

100: cell culture vessel; 101: projection; 102: culture section; 103: culture section side wall; 104: buffer section; 105: vessel material; 106, 117: mold; 107: culture solution; 108: cell; 109: cell adhering to the flat portion; 110: culture section substrate; 111: first mold matrix component; 112: second mold matrix component; 113: mold matrix; 114: replica material; 115: mold replica; 116: nickel sheet.

DETAILED DESCRIPTION OF THE INVENTION

The cell culture vessel of the present invention will be described in detail below with reference to the accompanying drawings.

Figure 1:
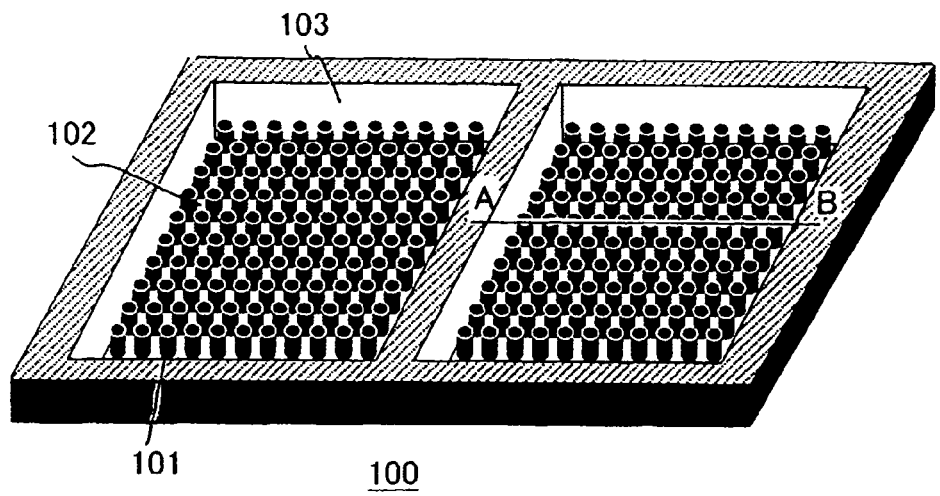
FIG. 1 is a schematic illustration showing a perspective view of one example of cell culture vessel according to the present invention.

FIG. 1 is a perspective view showing a first embodiment of cell culture vessel 100 according to the present invention. In the culture section 102 of the cell culture vessel 100 containing the cells and their culture solution, there are formed the projections 101 having an equivalent diameter smaller than the cells to be cultured. The equivalent diameter of these projections is 10 nm to 10 μm and their height is 10 nm to 1 mm. For reducing the contact area with the cells, the equivalent diameter of these projections is set to be sufficiently smaller than the cell diameter, for instance ⅕ or less of the cell diameter. The interval between the projections 101 needs to be less than the cell diameter. Thus, the projections are designed such that their sectional area will be smaller than the sectional area of the cells, and a plurality of these projections will exist within a section of the cell. Also, because of the necessity to let the culture solution infiltrate sufficiently into the lower portions of the projections 101, these projections are designed to have a sufficient height, such as equal to the equivalent diameter or greater, more preferably 5 or more times the equivalent diameter. From the viewpoint of structural strength, however, the height is preferably not more than 100 times the equivalent diameter. As for the culture section 102, although only one such culture section may be provided for one cell culture vessel 100, the section may be divided into two or more portions by the side walls 103 as shown in FIG. 1, which makes it possible to culture the cells under varied conditions with one cell culture vessel 100.

Figure 2A:
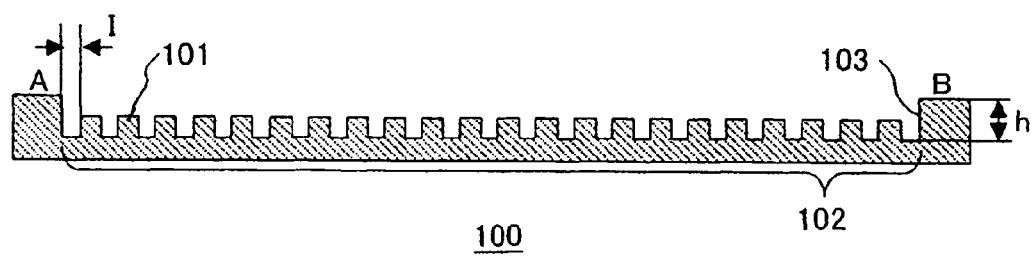
FIG. 2 is schematic illustrations showing the sectional views of one example of cell culture vessel according to the present invention.
Figure 2B:
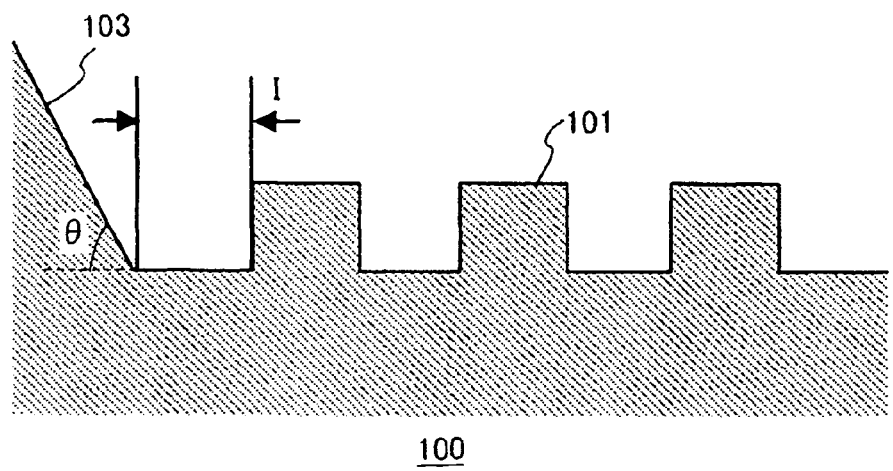

FIG. 2(*a*) is a schematic illustration showing the section cut along the line A-B in FIG. 1 in the first embodiment of cell culture vessel 100 according to the present invention, and FIG. 2(*b*) is a schematic illustration showing in particular the boundary between the culture section 102 and its side wall 103. The projections 101 are provided to a point close to the side wall 103 and substantially cover up the whole span of the culture section 102. The culture vessel is designed such that the distance I between an arbitrary position on the culture section/side wall boundary line and the nearest projection 101 will be not greater than the equivalent diameter of the cells to be cultured. The culture section 102 including the projections 101 is integral with the side walls 103, and they are made of a same material. It is most preferable to provide the projections 101 on the side walls 103, too, as this arrangement can further raise the effect of the projections 101. When such working is difficult, there may be provided a different surface structure to which the cells are harder to adhere than to the culture section 102, or a non-cell-adherent surface treatment may be applied. The culture section side wall 103 is preferably of the height that can hold the culture solution without allowing it to overflow from the surface of the culture section 102. This height can be properly determined in accordance with the shape and area of the culture section 102, its hydrophilicity and the amount of the culture solution supplied to the culture section 102, but preferably the height h of the side wall 103 from the culture section 102 is selected to be 0.05 to 100 mm. Also, the side wall 103 is preferably made higher than the projections 101 on the culture section 102, more preferably 10 or more times the height of the projections 101. This height depends on the configuration of the culture section 102, but its lower threshold is decided according to whether a proper amount of culture solution can be held on the culture section 102 having the projections 101, while the upper threshold is decided by the operatability with the culture solution or cells. The angle of inclination θ made by the side wall 103 with the culture section 102 is preferably selected to be not less than 45 degrees for preventing adhesion of the cells to the side walls 103. It is also possible where necessary to provide the stepped side walls to make it easier to form a specific surface structure for the side walls 103.

Figure 3:
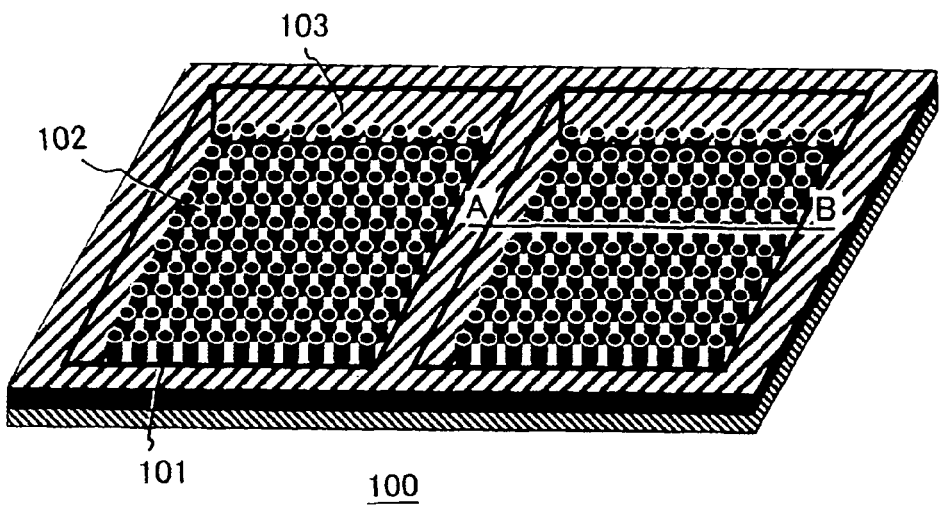
FIG. 3 is a schematic illustration showing a perspective view of another example of cell culture vessel according to the present invention.

FIG. 3 is a perspective view of the second embodiment of cell culture vessel 100 according to the present invention. The geometry of the projections 101 on the culture section 102 is the same as that in the first embodiment, but the side walls 103 are made of a material with lower adhesiveness to the cells than the culture section 102 and are bonded to the culture section 102. Bonding between the side walls 103 and the culture section 102 is made such that they can be detached from each other without harming the projections 101, which can facilitate post-culture observation.

Figure 4:
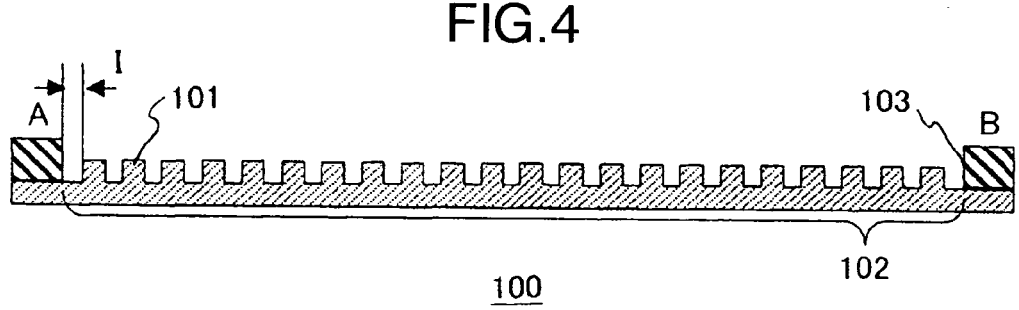
FIG. 4 is a schematic illustration showing a sectional view of another example of cell culture vessel according to the present invention.

FIG. 4 is a schematic illustration showing a sectional view taken along the line A-B in FIG. 1 in the second embodiment of cell culture vessel 100 according to the present invention. Like in the first embodiment, the projections 101 are formed to a point close to the side wall 103 and cover up substantially the entirety of the culture section 102. The vessel is designed such that the distance I between an arbitrary position on the culture section/side wall boundary line and the nearest projection 101 is not greater than the equivalent diameter of the cell to be cultured.

Figure 5:
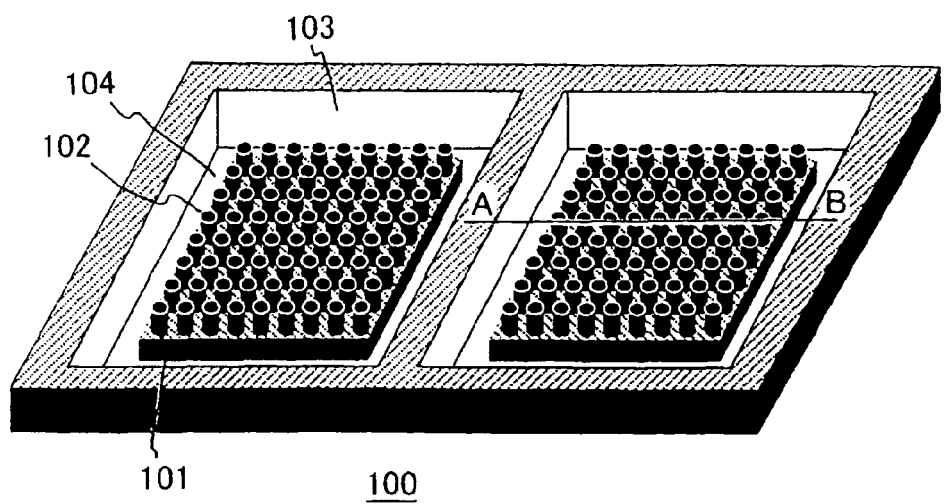
FIG. 5 is a schematic illustration showing a perspective view of a third example of cell culture vessel according to the present invention.

FIG. 5 is a perspective view showing the third embodiment of cell culture vessel 100 according to the present invention. The geometry of the projections 101 on the culture section 101 are the same as those in the first and second embodiments, but in the instant embodiment a buffer section 104 is provided between the culture section 102 and the side walls 103, said buffer section 104 surrounding the culture section 102 and disposed at a lower position than the culture section 102. Even when the cells are adsorbed on the side walls 103, it is possible, because of the presence of said buffer section 104, to prevent the adsorbed cells from transferring to the culture section 102.

Figure 6:
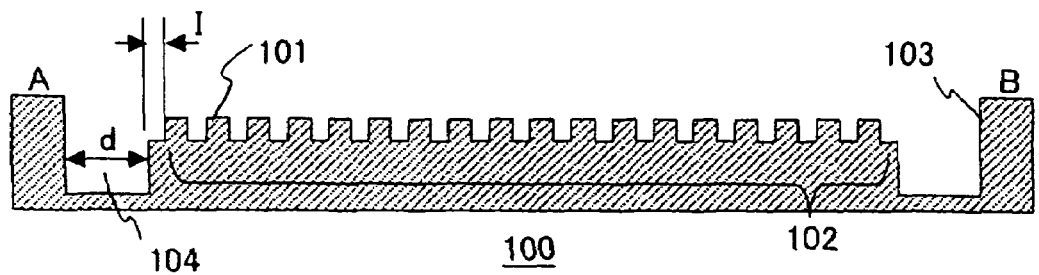
FIG. 6 is a schematic illustration showing a sectional view of the third example of cell culture vessel according to the present invention.

FIG. 6 is a schematic illustration showing a sectional view taken along the line A-B in FIG. 1 in the third embodiment of cell culture vessel according to the present invention. The projections are provided to a point close to the buffer section 104 and cover up substantially the entirety of the culture section 102. The vessel is designed such that the distance between the buffer section side edge of the culture section 102 and the nearest projection 101 is not greater than the equivalent diameter of the cell to be cultured. The buffer section 104 is of a depth sufficient for preventing the cells which moved onto the buffer section 104 from further transferring to the culture section 102. This depth, although variable depending on the type of the cells to be cultured and the culturing conditions, has a height of 0.01 mm or greater from the culture section 102 and is smaller than the height of the side wall 103 for allowing the culture section 102 to be submerged in the culture solution. The width d of the buffer section (distance from the side wall to the edge of the culture section) is preferably made greater than the equivalent diameter of the cells to be cultured for preventing the cells from transferring to the culture section 102.

The material of the cell culture vessel 100 according to the present invention is not specifically defined, but it is selected in consideration of desired working precision, surface properties, optical properties, strength and other factors of the vessel to be made. Specifically, there can be used thermoplastic resins such as polyethylene, polypropylene, polyvinyl alcohol, polyvinylidene chloride, polyethylene terephthalate, polyvinyl chloride, polystyrene, ABS resins, AS resins, acrylic resins, polyamides, polyacetal, polybutyrene terephthalate, glass-reinforced polyethylene terephthalate, polycarbonates, modified polyphenylene ethers, polyphenylene sulfide, polyether ether ketone, liquid crystalline polymers, fluorine resins, polyarylates, polysulfone, polyether sulfone, polyamide-imide, polyether-imide and thermoplastic polyimides, thermosetting resins such as phenol resins, melamine resins, urea resins, epoxy resins, unsaturated polyester resins, alkyd resins, silicone resins, diallyl phthalate resins, polyamide-bismaleimide and polybisamide-triazole, and mixtures of two or more of these resins. It is also possible to use inorganic materials such as glass. Since the material used for the cell culture vessel 100 is usually required to have affinity for the cells, it needs to confirm affinity for the cells to be cultured before selecting the material. Also, in order to facilitate culture evaluation, it is preferable to use a material which can be regarded as transparent to the light of a wavelength used for the observation and which substantially does not emit fluorescent light in the same wavelength region. For instance, by using biodegradable resins including aliphatic polyesters or polyacid anhydrides such as polylactic acid and polycaprolactone, synthetic materials such as synthetic polypeptide and natural materials such as chitosan and cellulose, it is possible to make a cell culture vessel which allows easy biodegradation of the culture.

The material of the projections 101 in the present invention is also not specifically defined, but as in the case of vessel material, the above-mentioned resin compositions or inorganic materials such as glass may be used in consideration of desired working precision, surface properties, optical properties, strength and other factors. These projections are preferably formed integral with the culture section 102.

Figure 7A:
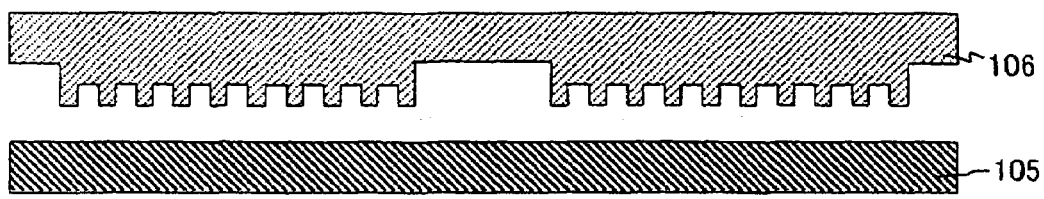
FIG. 7 is schematic illustrations showing the production process of a cell culture vessel according to the present invention.
Figure 7B:
Figure 7C:
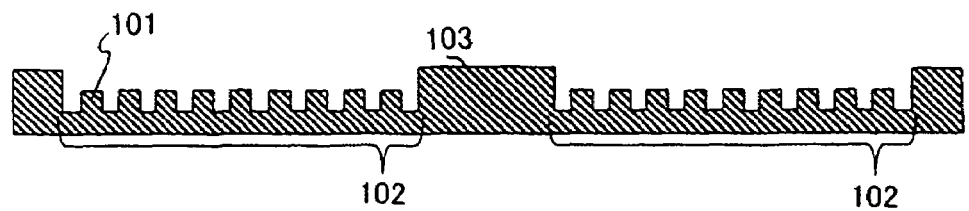
Figure 8A:
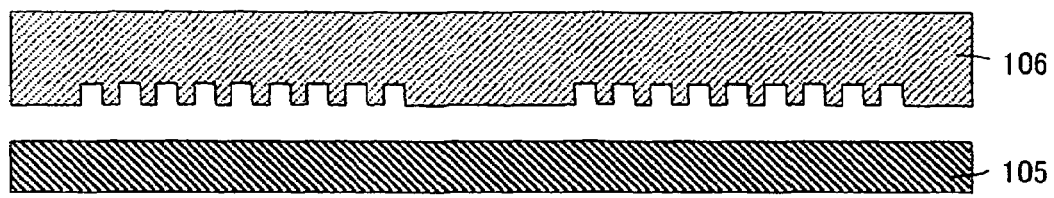
FIG. 8 is schematic illustrations showing the production process of another cell culture vessel according to the present invention.
Figure 8B:
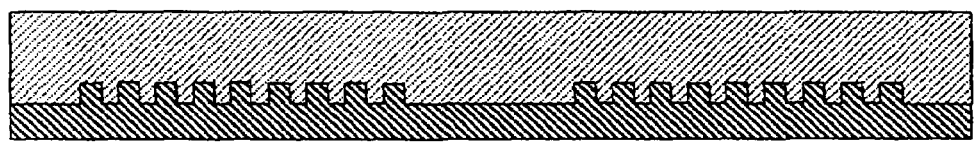
Figure 8C:
Figure 8D:
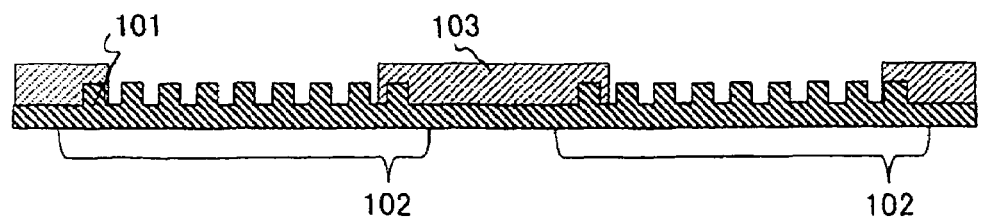

A process for forming the first embodiment of cell culture vessel 100 according to the present invention is shown in FIG. 7. In this embodiment, so-called nano-imprinting techniques are used for forming the vessel 100. The vessel base material 105 is softened by heating, and a mold 106 having a geometry defining the projections 101, culture section 102 and its side walls 103 is pressed against the softened vessel base material to transfer the geometry of the mold to the vessel base material, thereby obtaining a cell culture vessel 100 having the projections 101, culture section 102 and its side walls 103.

FIG. 8 shows a process for making the second embodiment of cell culture vessel according to the present invention by using nano-imprinting techniques. The vessel base material 105 is softened by heating, to which a mold 106 having a geometry defining the projections 101 and culture section 102 is pressed to transfer the geometry of the mold 106 to the vessel base material 105. Then the separately formed culture section side walls 103 are joined to the culture section 102 to make a cell culture vessel.

Figure 9A:
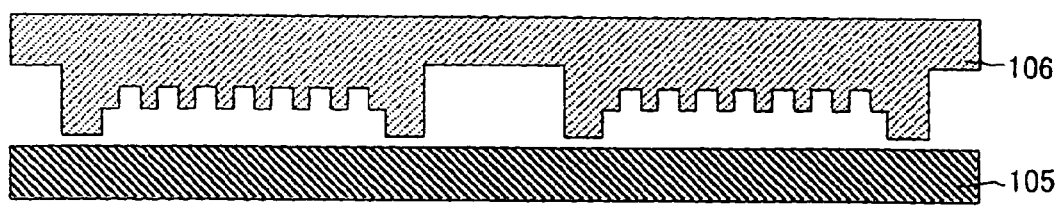
FIG. 9 is schematic illustrations showing the production process of a third cell culture vessel according to the present invention.
Figure 9B:
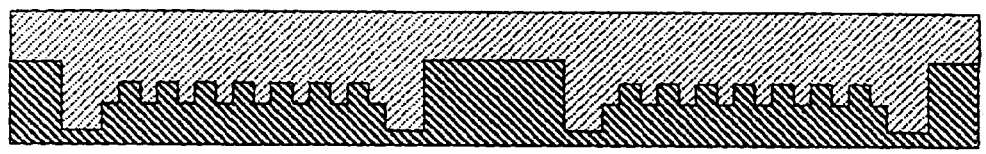
Figure 9C:
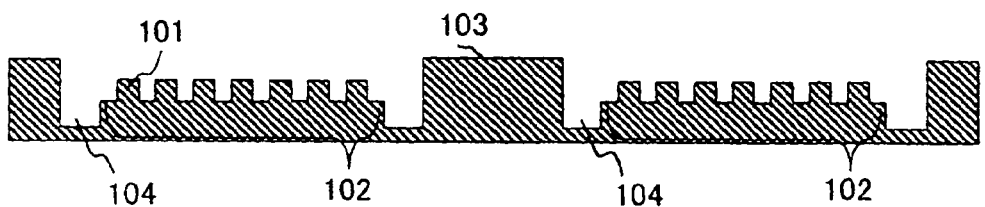

FIG. 9 shows a process for forming the third embodiment of cell culture vessel 100 according to the present invention by using nano-imprinting techniques. The vessel base material 105 is softened by heating, and a mold 106 having a geometry defining the projections 101, culture section 102, its side walls 103 and buffer section 104 is pressed to said softened base material 105 to transfer the mold geometry to the vessel base material 105 to obtain a cell culture vessel 100 having the projections 101, a culture section 102, its side walls 103 and a buffer section 1

In the above processes for constituting the first to third embodiments of cell culture vessel, it is possible to employ a high aspect ratio nano-imprinting method which makes it possible to form the projections 101 with a shape of a higher aspect ratio than the mold 106 by drawing the vessel base material 105 filled in the shape corresponding to the projections 101 in the mold when the mold is separated from the vessel base material 105 after pressing.

The molds 106 used for forming the respective cell culture vessels 100 described above are required to have a shape corresponding to the projections 101 to be formed on the vessel, that is, they need to be have on their surface a configuration which is 10 nm to 10 μm in equivalent diameter and 100 nm to 1 mm in height. To meet this requirement, the molds contain at least one of metal, inorganic material such as carbon and silicon, and resin composition, and their surface geometry is formed by fine working such as photo-lithography, electron-beam direct writing, corpuscular beam working and scanning probe working, self-organization of fine particles, etc., or formed by conducting shape transfer, by such method as nano-imprinting, injection molding or electroless plating, from the master made by using the above-said techniques. The shape defining the culture section side walls 103 is of macro-scale as compared with the fine geometry of the projections 101, and in such a case, it is possible to form the molds 106 with high precision by employing machine working jointly with the techniques for joining the plural molds. It is also possible to afford non-cell-adhesiveness to the culture section side walls by applying fine working on them by combining the macro-shape defining technique with photo-lithography with large depth of focus, laser working or self-organization of corpuscles. In FIGS. 7 to 9, as the method for forming the projections 101, there is used a so-called nano-imprinting method in which the mold 106 is pressed to the softened vessel base material 105, but obviously it is also possible to employ other methods, for example, resin molding such as injection molding or direct working such as laser working without using the mold.

In the present invention, the cell culture vessel is subjected as desired to a surface treatment necessary for cell culture, for example, dipping in a solvent containing an oxidizing agent such as hydrogen peroxide or ozone, ultraviolet irradiation, hydrophilicity treatment such as vapor-phase plasma treatment, coating with a protein such as polylysine, albumin, collagen, fibronectin, fibrinogen, vitronectin and laminin by dipping in a solution or other means, plating, metal coating by vapor phase deposition, or surface modification by irradiation with light, electron rays or corpuscular beams. Further, it is possible to apply a surface treatment to the top end portions of the projections 101 or the culture section side walls 103 alone, if necessary with an in-plane distribution, by conducting such treatments as stamping with an elastic material such as silicone rubber, resin film or metallic film, heating by use of a partial dispensing method, or partial coating with a solvent containing a hydrophobic agent such as resin paste, silicone grease or fluorine coating agent or a protein.

The culture section side walls in the embodiments shown in FIGS. 3, 4 and 8 are formed by machining, molding or other means separately from the culture section 102 described above. The material of these side walls is selected from those mentioned above for use for the cell culture vessel 100. If the side walls 103 are formed with the same material as used for the culture section 102, there can be obtained a structure with high geometrical precision and strength after joining and a visual appearance shown in FIG. 1. For joining these side walls 103 and culture section 102, there can be used high-precision joining means such as pressing under heating, heat fusion such as vibratory fusion or infrared laser fusion, and use of an adhesive. In heat fusion, however, it is necessary to select the conditions that would not cause deformation of the projections 101 on the culture section 102 beyond the allowable range. In case of using an adhesive, it is essential to select the conditions under which the adhesive is not allowed to transfer to the surface of the culture section 102 during the joining operation, the cells won't be adsorbed on the surface after curing, and the elute does not show cytotoxicity. By forming the culture section side walls 103 with a material having elasticity and high adhesiveness to the cell culture vessel 100, there can be obtained a sufficient adhesive strength by merely attaching the side walls 103 tightly on the cell culture vessel 100. Also, by forming the side walls 103 in this way, it is possible to obtain a structure in which the side walls 103 can be detached without harming the projections 101 and the cells cultured thereon, which can facilitate the observation work after culture. In order to narrow down the space between the culture section side walls 103 and the projections 101 on the culture section 102, it needs to do in advance high-precision positioning of the projections 101 and the side walls 103. For this purpose, as shown in FIG. 8(d), the region where the projections 101 are formed is made larger than the culture section 102 so that only the projections 101 immediately below the side walls 103 will be smashed when joined, or the projections 101 will be covered up with the lower portions of the side walls 103, whereby it is possible to reduce the distance between the projections 101 remaining on the culture section 102 and the culture section side walls 103.

The cell culture vessel 100 may have two or more culture sections 102, and in use thereof, such culture sections 102 may be separated from each other and used for different modes of culture. Also, obviously a part of the cell culture vessel 100 which may hinder the culture operation can be cut away. Such cutoff is facilitated if the vessel 100 is provided in advance with a means that is helpful for making such cutoff, for example providing a line of notches or cutouts along which an unnecessary vessel part can be cut away with ease as by bending.

The cell culture vessel 100 of the present invention has to be transported, after production, to a site where the cells are actually cultured. During such transport, it is required to prevent the vessel from being contaminated with foreign matter such as dust and bacteria. For this purpose, it is necessary to incorporate a vessel packaging step for isolating the culture section 102 from the outside, by for instance putting the whole vessel 100 in a pouch and heat sealing its opening, or attaching a cover film to cover only those portions of the culture section 102 and its side walls 103 which will be brought into contact with the culture solution in the culturing operation. It is also desirable to conduct a sterilization treatment for killing the microorganisms remaining on the culture section 102 after packaging. Exemplary of such sterilization treatment is autoclaving using high-temperature steam, but this method involves a possibility to cause deformation or denaturation of the product by high-temperature steam depending on the material of the vessel 100 or configuration of the projections 101. Therefore, it is advisable to apply a sterilization treatment, such as ultraviolet-light irradiation, ethylene oxide gas sterilization or gamma-ray sterilization, which can be carried out at a temperature lower than the glass transition point of the material composing the vessel. Of course, autoclaving can be employed in case a heat-resist resin or glass is used as vessel material. The sterilization treatment is usually conducted after packaging, and vapor-permeable type packaging is adopted depending on the sterilization method used. In such packaging, it is also recommendable to adapt an indicator which can indicate whether the necessary treatment has been done or not by reacting to the particular treatment.

Figure 10:
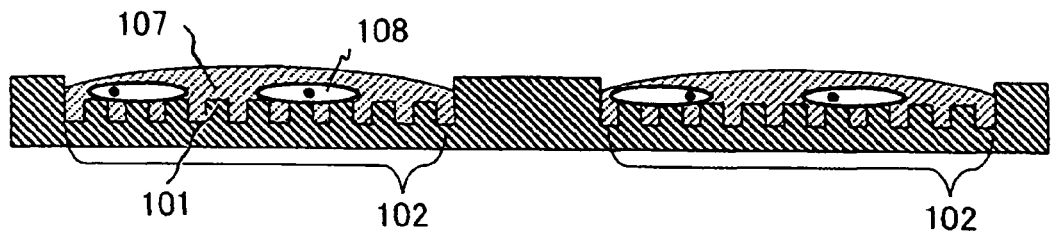
FIG. 10 is a schematic illustration showing a mode of use of a cell culture vessel according to the present invention.
Figure 11:
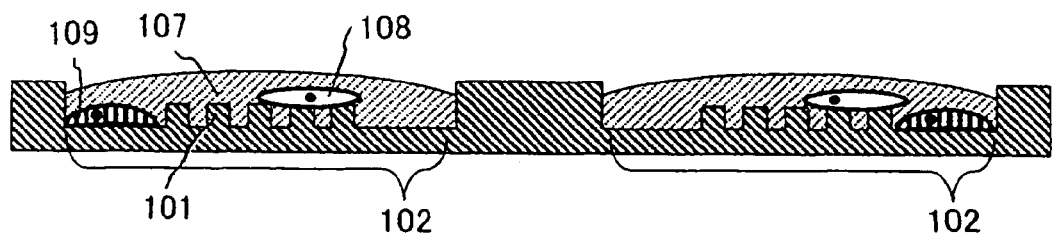
FIG. 11 is a schematic illustration showing cell culture in a cell culture vessel having a region devoid of projections in the culture section.

FIG. 10 illustrates a mode of use of a cell culture vessel 100 according to the present invention. The culture section 102 is filled with a culture solution, and the cells 108 are placed on the projections 101 and cultured in the ordinary way. In the cell culture vessel 100 of the present invention, the mode of contact between each cell 108 and the culture section 102 is point contact because of the presence of the projections 101, so that it is possible to prevent the cells 108 from being damaged when separated. Also, by varying the geometry and surface treatment of the projections 101 depending on the type of cell to be cultured, it is possible to form the high-quality cultured cells without causing damage during separation. Further, in the cell culture vessel according to the present invention, since the projections 101 are arranged so as to cover up substantially the entirety of the culture section 102, there exist no cells adhering to the flat portion of the culture section 102 unlike in the type of the vessel having the flat portion along the edge as shown in FIG. 11, so that the cell culture improving effect of the projections 101 is enhanced. Moreover, by substantially eliminating the region of flat portion where the cells 108 are liable to adhere to the culture section 102, and, in some cases, by incorporating a structure which can prevent the cells 108 from being adsorbed to the culture section 102 and, should they be adsorbed, can prevent the adsorbed cells from being positioned on the culture section 102, there can be obtained an additional effect to prevent mixing of the cells cultured at the area having no projections when the projections 101 give a specific influence to the cells 108. In the present invention, the "cell 108" is a concept including the organized cultured cells represented by cultured tissue and organ cells.

In use of the cell culture vessel 100 according to the present invention, culture is carried out with the culture solution 107 and cells 108 being placed on the culture section 102 in a thermostatic culture tank in the conventional way, and there are conducted as required such operations as changing of the culture solution 107, taking-out of the cells 108, supply of the reagents, shaking, observation by a microscope, and in some cases freezing in a freezer. During these unit operations, the culture vessel must be transferred from one operating unit to another. It is necessary to prevent the culture vessel from being deflected to cause biasing of the culture solution 107 or cells 108 or their leakage from the culture section 102 during the above-said operations or transfer, so that it is desirable that the culture vessel 100 has sufficient rigidity as a whole. Therefore, at least the peripheral portion of the vessel and part of the region other than the culture section 102 are preferably constructed to have rigidity with a thickness of not less than 0.5 mm. In order to alleviate extinction or fluorescence in the members composing the culture section 102 and encourage conduction of temperature from the outside, the culture section 102 may be designed to be smaller in thickness than the peripheral portion. Also, for providing a lightweight and high-rigidity structure, the portions having no bearing on strength or handling qualities may be excluded by, for instance, forming a region for reinforcing strength by bending an edge of the vessel, or making hollow the side wall 103 on the side opposite from the culture section 102. Further, in case the culture vessel does not have enough rigidity in itself, a separately prepared member or members having rigidity may be adapted to the vessel after forming the culture section 102 to thereby afford desired rigidity to the vessel.

DESCRIPTION OF PREFERRED EMBODIMENTS

The present invention is further illustrated by the following embodiments.

Example 1

Figure 12:
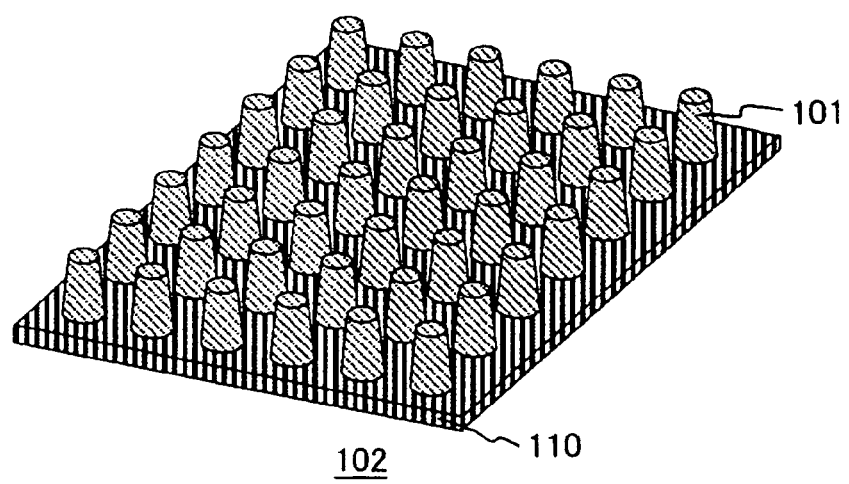
FIG. 12 is a schematic illustration showing a scanning electron microphotograph of the projections in the present invention.
Figure 13A:
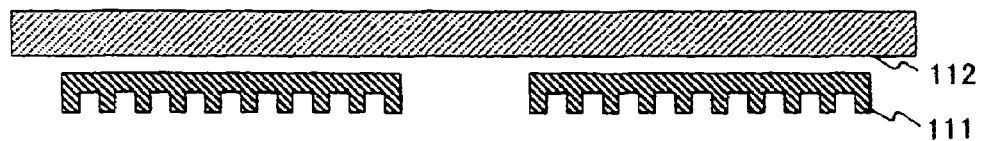
FIG. 13 is schematic illustrations showing the production process of a mold in the first embodiment.
Figure 13B:
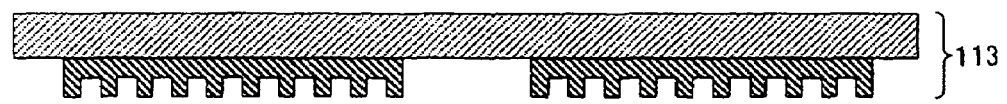
Figure 13C:
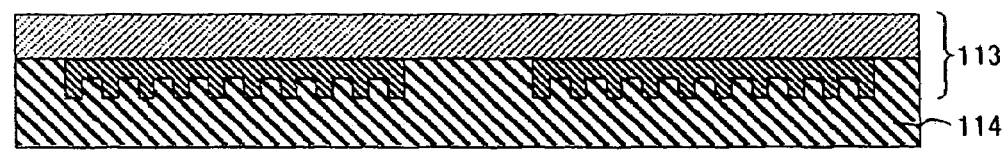
Figure 13D:
Figure 13E:
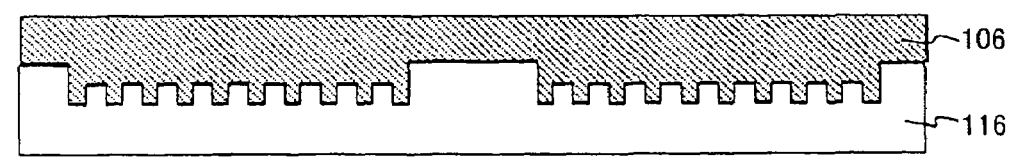
Figure 13F:

An embodiment of the present invention is described below. FIG. 12 is a schematic illustration of s scanning electron microphotograph of the culture section 102 made according to the instant embodiment. The culture section 102 is furnished with a plurality of projections 101 which are made of polystyrene having a molecular weight of 2,000 to 3,840,000. The upper limit of the molecular weight can be extended up to 6,000,000.

These projections 101 are of a columnar configuration measuring 500 nm in diameter at the bottom and 1 μm in height. So, the ratio of height to one side of the columnar projection is 2, or greater than 1. The interval between the adjoining projections is 1 μm, which is smaller than the diameters of the ordinary cells. The projections 101 are arrayed in a two-dimensional square arrangement as shown in FIG. 12.

The diameter at the top end of each projection is 400 μm, that is, the projection is diminished in diameter toward the top end. In this embodiment, each projection tapers off toward its top end, but the same effect can be obtained by designing each projection as a column having no reduced-diameter portions (constrictions) or to have a mushroom-like shape which tapers off toward the top end but has a bulge at the top end.

Each projection 101 is made of polystyrene same as the culture section substrate 110, and they are connected to each other to form an integral structure.

The shape of the projections 101 tapering off toward the top end from the bottom end has the effect of securing the projections against coming off the culture section substrate 110. As the projections 101 are made of the same material as and integrated with the substrate 110, they are additionally ensured against coming off the substrate.

While polystyrene is used as the material of both projections 101 and culture section substrate 110 in the present embodiment, it is possible to select other material from those exemplified above as usable materials of the cell culture vessel 100 in accordance with the type of the cells to be cultured and the way of use of the vessel 100. In the embodiments shown later, the projections 101 and the substrate 110 of culture section can be produced through the similar process by properly changing the conditions in accordance with the material used.

FIG. 1 is a schematic illustration of the cell culture vessel 100 produced in the instant embodiment. This cell culture vessel 100 is made, in its entirety, of polystyrene having a molecular weight in the above-defined range, and comprises a culture section 102 provided with the projections 101 and the culture section side walls 103. The culture section 102 is square-shaped with its one side measuring 1 cm. The culture section side walls 103 are erected substantially vertically to enclose the culture section 102 and measure 0.7 mm in height. There are provided two culture sections 102 separated at the center of the culture vessel 100 and spaced apart 5 mm from each other.

The above cell culture vessel 100 was made in the following way. FIG. 7 illustrates a production process of the cell culture vessel 100 in the instant embodiment. In this process, the cell culture vessel 100 was formed by the nano-imprinting method. The vessel base material 105 (20 mm×40 mm, 1 mm thick) comprising polystyrene mentioned above was heated to 150° C. and thereby softened, and a nickel-made mold 106 having a geometry defining the projections 101, culture section 102 and culture section side walls 103 was pressed to the softened vessel base material 105 under a pressure of 4 MPa for 180 seconds. Then, with the pressure of the press unreleased, the whole assembly was cooled to 35° C., after which the mold 106 and vessel base material 105 were taken out and the mold 106 was separated by lifting it up vertically from the vessel base material 105 to thereby obtain a cell culture vessel 100 having the projections 101, culture section 102 and culture section side walls 103.

A production process of the mold 106 is shown in FIG. 13. The first mold matrix component 111 shown in FIG. 13(a) is a both-side polished silicon wafer with 1 cm square crystal orientation (100) having a geometry defining the projections 101, culture section 102 and culture section side walls 103, and the second mold matrix component 112 is a flat 20 mm×40 mm anode-joining glass plate defining the shape of the topmost portions of the culture section side walls 103 and other regions. In the first mold matrix component 111, a fine concave and convex configuration corresponding to the projections 101 on the cell culture vessel 100 is formed by photo-lithography. This component was cut out with the specified size from a 20 mm-diameter silicon wafer and cleaned. Then, the first and second mold matrix components 111 and 112 were joined by the anode joining method (400° C., 1 kV) as shown in FIG. 12(*b*) to make a mold matrix 113. The height of the culture section side walls 103 is decided by the height of the mold matrix component 111, but its height can be varied by suitable means such as placing a specified spacer between the first and second mold matrix components 111 and 112. Adjustment of height can be made over a wider range if the second mold matrix component 112 is provided with a geometry defining at least a part of the culture section side walls 103. Various mold matrix component joining methods other than said anode joining method, such as methods for forming metallic or inorganic or organic adhesive layers and welding, can be selected depending on the material of said spacer or mold matrix components, flatness and configuration of the interface of joining to enhance working precision. A fluorine type release agent was applied to the mold matrix 113, and as shown in FIG. 13(*c*), a 20 mm×40 mm, 2 mm thick polystyrene-made replica material 114 was pressed under 10 MPa at 150° C. and, after cooling, the mold matrix 113 was separated to obtain a mold replica 115. A nickel coating film was formed on said mold replica 115 by electroless plating, and then electroplating was carried out thereon to increase the nickel coating thickness to 3 mm, thereby fabricating a mold 106. Thereafter, fluorine type release treatment was conducted on the region including the portions defining the projections 101, culture section 102 and culture section side walls 103 in the mold.

It is preferable to make the mold 106 with a resin having high heat resistance and strength by using nano-imprinting or casting techniques used for forming the replica, instead of said plating method, as the mold making process can be simplified as compared with when using the plating method. In case of making a trial product in a small quantity, the mold matrix 113 may be used directly as the mold 106.

In this embodiment, the mold 106 is additionally provided with a shape corresponding to the buffer section 104 between the culture section 102 and its side walls 103, said buffer section 104 surrounding the culture section 102 and disposed at a lower position than the culture section 102, to provide the structure presented as the third embodiment of the present invention.

In the present invention, a 1 mm thick vessel base material 105 comprising polystyrene is used, but it is necessary to provide an optimal thickness in accordance with the desired area of the culture section 102 and the desired height of the culture section side walls 103. For instance, in the case of a cell culture vessel having a larger culture section than in the instant embodiment, the thickness of the peripheral portion of the vessel or the culture section must be made greater than 0.5 mm for maintaining rigidity of the whole vessel in handling thereof. Actually, however, the thickness of the vessel base material 105 needs be selected to be optimal in balance with rigidity by taking into account the space held by the whole vessel and its operatability. In case the culture sections 102 are designed the mutually separated 16 mm diameter circles (corresponding to 24-well microplate), 8 mm diameter circles (corresponding to 96-well microplate), 4 mm diameter circles (corresponding to 384-well microplate) or 2 mm diameter circles (corresponding to 1,536-well microplate) as in the widely used microplates, the thickness of the culture section 102 and the thickness of the culture section side walls 103 can be made smaller than 0.5 mm. Even in these microplates, as it is required to maintain sufficient rigidity of the whole vessel, it is preferable to have a region, for example an edge of the microplate or a portion between the culture sections, where the thickness is not less than 0.5 mm. In order to afford such rigidity, a reinforcement such as outer frame or backing may be separately provided on the culture vessel 100 after forming the culture sections 102. Particularly when the culture vessel is designed to have a configuration like a microplate, the height of the side walls 103 in each culture section 102 is made around 1 cm in many cases, but it can be changed according to the area of the culture sections 102. Especially in case the area of the culture section 102 is small as when it was designed correspondent with a 384-well microplate or 1,536-well microplate such as mentioned above, the height of the culture section side walls 103 can be made even smaller as the required amount of the culture solution is lessened to about 1 to 100 µl.

The shape of the culture section 102 is most preferably circular for preventing stagnation of the culture solution in the culture section 102, but in the present embodiment, the culture section 102 was shaped square for facilitating dicing of the first mold matrix component 111 on the mold 106. The shape of the culture section, however, is not specified in the present invention; it may be elliptical, polygonal or otherwise shaped according to the culturing method, production process and arrangement of the culture section 102 on the cell culture vessel 100. The size of the culture section 102, its depth and the number of the culture sections on one cell culture vessel 100 may be decided to be optimal according to the cell line to be cultured and the purpose of use of the culture. For instance, the culture section 102 is preferably enlarged in case the cell culture vessel 100 is used for obtaining a relatively large culture organization or a plurality of cultured cells of the same condition, but the culture section 102 needs be rather reduced in size in case the culture vessel is used for culturing the cells for making experimental assays under multiple conditions. If the culture vessel has a geometry like a microplate having many separated culture sections in one vessel, it is possible to lessen the amount of the reagents or the number of the cells used for the cultured. Also, by changing the surface treatment of the projections 101 in the culture section 102, shape of the top ends of the projections and their size (diameter, height, etc.) and arrangement for each of the separated regions according to the purpose of use of the culture, it is possible to test the change of condition of the cultured cells by the shape and arrangement of the projections 101 when a same type of cells are cultured under the same conditions, and to decide the optimal pattern of projections 101 for each type of cells when different types of cells are cultured. Also, by changing the shape and arrangement of the projections 101 in a culture section 102, it is possible to use the device for such purpose as search for the projection pattern optimal for the cells to be cultured by testing the change of condition of the cultured cells by using one culture section 102 alone.

Example 2

Figure 14:
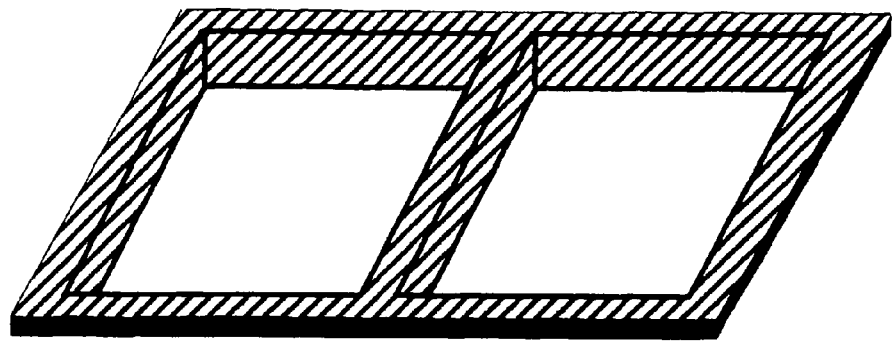
FIG. 14 is a schematic illustration showing a perspective view of the culture section side walls in the second embodiment.
Figure 15A:
FIG. 15 is schematic illustrations showing the production process of a culture section side wall in the second embodiment.
Figure 15B:
Figure 15C:
Figure 15D:

Another embodiment of the present invention is described below. FIG. 2 is schematic illustrations of the cell culture vessel 100 produced in the instant embodiment. In this cell culture vessel 100, the culture section 102 including the projections 101 is composed of polystyrene of the same molecular weight as that used in the first embodiment, and the culture section side walls 103 are made of PDMS (poly(dimethyl siloxane) produced by Dow Corning Co., Ltd.) and have the geometry shown in FIG. 14 with a height of 0.7 mm. The culture section 102 is square with each side measuring 0.90 cm, and the side walls 103 are erected substantially vertically enclosing the culture section 102. There are provided two culture sections 102 divided at the center of the culture vessel 100 and separate 5 mm from each other. The projections 101 formed on each culture section 102 are of a cylindrical shape measuring 500 nm in diameter at the lower end and 1 µm in height and have the same construction as those in the first embodiment.

The above cell culture vessel 100 was produced in the following way. FIG. 8 illustrates a production process of the cell culture vessel 100 in the present embodiment. The aforementioned vessel base material 105 (20 mm×40 mm×1 mm thick) comprising polystyrene was softened by heating to 150° C., and a nickel-made mold 106 having a geometry defining the projections 101 and culture sections 102 (1 cm square) was pressed to the softened vessel base material under pressure of 4 MPa for 180 seconds. Then, with the pressure kept unreleased, the whole unit was cooled to 35° C., the mold 106 and the vessel base material 105 were taken out, and the mold 106 was separated from the vessel base material 105 lifting the mold vertically from the vessel base material, thus forming the projections 101 and the culture sections 102. Then the PDMS-made side walls 103 shown in FIG. 14, which had been formed by casting from a separate mold, were attached tightly to the culture sections 102 to obtain a cell culture vessel 100.

The mold production process is the same as in the first embodiment, but since the culture section side walls 103 are joined later to form the vessel, there is no need of providing a corresponding configuration to the related part of the mold 106. It is however possible to give to the mold a configuration corresponding to the lower part of the side wall 103 for the purpose of supplementing the height of the side wall. A mold is also used for forming the side walls 103, and this mold is in many cases made of such metal as iron or nickel, but it is possible to form the mold from an organic resin, silicon wafer or an inorganic material such as glass to meet the requirements for working precision, simplicity or visibility. For making the mold for forming the culture section side walls 103, a suitable method is selected from those shown above for producing the mold 106 used for making the cell culture vessel 100 according to working precision required and the mold material used.

A process for forming the culture section side walls 103 in the instant embodiment is illustrated in FIG. 15. In this embodiment, a 2 mm thick nickel plate was machined into a mold 117 with a geometry having the convex portions measuring 0.90 cm in one side and 1 mm in height corresponding to the side wall 103. A fluorine type mold release treatment was conducted on the surface of the mold, then the non-cured PDMS was mixed with a curing agent, and an amount thereof for providing a height of 0.7 mm was cast into the mold 117, followed by a heat treatment at 120° C. for 10 minutes to cure PDMS, after which the molding was separated from the mold to obtain the culture section side walls 103. The thus formed PDMS-made culture section side walls 103 were low in adhesiveness to the cells and suited for use in the cell culture vessel 100. Also, because of high adhesiveness of the PDMS-made culture section side walls 103 to the culture section 102, there can be obtained air tightness required for culture by correctly disposing and tightly attaching the side walls 103 at the prescribed positions on the culture section 102. The projections 101 on the culture section 102 are formed in a 1 cm² square region as mentioned above, so that by arranging the side walls 103 to cover a portion of 0.05 cm at the edge of the culture section 102, it is possible to make the distance between each side wall 103 and the nearest projection 101 1 µm same as the interval between the projections. Also, after culturing the necessary cells, the culture section side walls 103 can be removed with ease by detaching them from the culture section 102 after removing the culture solution. Thus, in the cell culture vessel according to the present invention, it is possible to remove the culture section side walls 103 which may become an obstacle to the cultured cell observation, so that the cell culture vessel of the present invention is suited for high-resolution observation by an erect optical microscope or form evaluation of the cultured cells by a scanning electron microscope.

In this embodiment, as in the first embodiment, the size and depth of the culture sections 102 and the number of the culture sections on one cell culture vessel can be optimized according to the cell line to be cultured and the purpose of use of the culture. For instance, the culture sections 102 are preferably enlarged in case the cell culture vessel 100 is used as production means for obtaining plenty of cultured cells under the same condition, but the culture sections 102 are preferably reduced in size in case the culture vessel is used for culturing the cells for the purpose of making experimental assays under multiple conditions. If the cell culture vessel has a geometry like a microplate having many culture sections in one vessel, it is possible to reduce the amount of the reagents and the number of the cells used for culture.

Example 3

Described here is an instance where a surface treatment suited for cell culture has been applied on a cell culture vessel according to the present invention. An oxygen plasma treatment (100 W, 30 sec.) was applied as a hydrophilicity treatment on the cell culture vessel 100 having the projections 101 formed by the method of Example 1. A surface-hydrophilized PDMS-made flat stamp coated with 50 µg/mL of a collagen I solution (trade name: Cultrex, a bovine collagen I; solvent: 0.02M acetic acid solution) to a coating thickness smaller than the height of the projections 101 was attached tightly to the top ends of the projections 101 in the cell culture vessel 100 so that the collagen I solution would be applied to the top ends alone of the projections 101. After removing the flat stamp, the vessel was kept at room temperature for one hour and washed with PBS (phosphate buffer solution), thus modifying the top ends alone of the projections 101 with collagen I to effectuate a surface treatment suited for cell culture.

In the instant embodiment, after forming the projections 101, modification is conducted with collagen which is a kind of protein, but it is possible to apply any other suitable surface treatments according to the type the cells to be cultured and the material of the cell culture vessel 100 and the projections 101, such treatments including ultraviolet-light irradiation, hydrophilicity treatments such as dipping in hydrogen peroxide or ozone solution, introduction of functional groups such as amino group, carboxyl group, methyl group and $CF_3$ group, and coating with proteins such as polylysine, albumin, collagen, fibronectin, fibrinogen, vitronectin and laminin. Such a surface treatment may be applied to a part alone of the projections 101 to control the form of the cells to be cultured.

Example 4

An exemplification of the improvement of cell separatability after culturing the cells by using a cell culture vessel according to the present invention is shown below.

Figure 16:
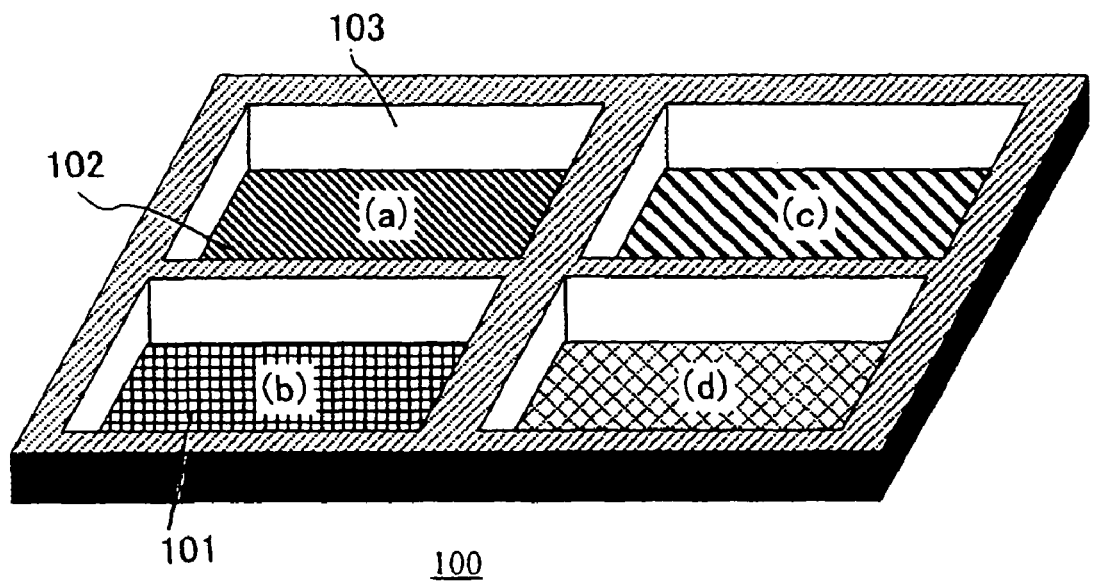
FIG. 16 is a schematic illustration showing a perspective view of the cell culture vessel in the fourth embodiment.
Figure 17:
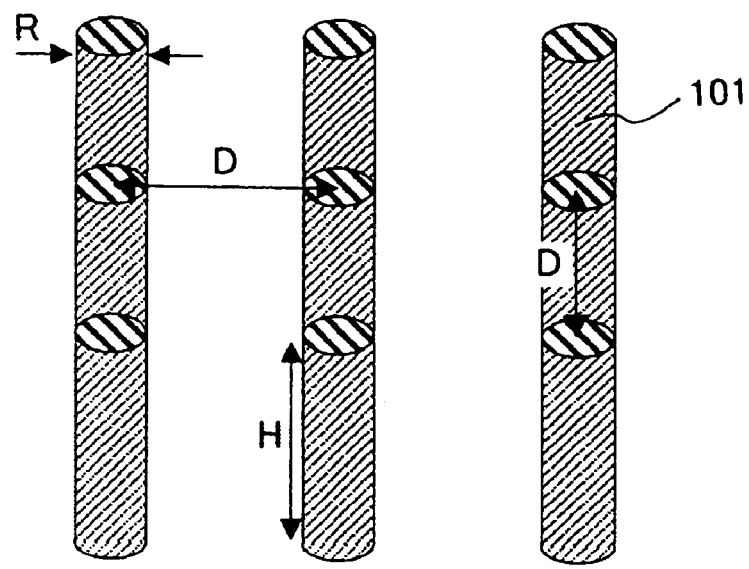
FIG. 17 is schematic illustrations showing scanning electron microphotographs of the projections in the fourth embodiment.

FIG. 16 is a perspective view of a cell culture vessel 100 made in the instant embodiment according to the method of Example 1, and FIG. 17 shows an example of arrangement of the projections 101 formed on the cell culture vessel 100. In this embodiment, in order to examine the relationship between separatability of the cultured cells and configuration of the projections 101 on the culture sections 102, there were formed in the vessel 100 four culture sections 102 in which the diameter R of the projections 101 was (a) 180 nm, (b) 240 nm, (c) 500 mm and (d) 2 μm, respectively. The height H of the projections 101 was 1 μm in all of the culture sections. Arrangement of the projections 101 was two-dimensional square lattice-like array as shown in FIG. 17, with the distance D between the adjoining projections 101 being twice the diameter R. These projections 101 were formed on each culture section 102 successively to a point close to the culture section side wall 103.

For the evaluation of cell separatability, the human mesenchymal stem cells (Cyro hMSC No. 2051 available from Cambrex Co., Ltd.) were seeded in a medium (Bullet Kit MSCGM (mesenchymal stem cell growth medium) available from Cambrex Co., Ltd.)) on each culture section 102, and cultured in a 37° C. and 5% $CO_2$ incubator for 5 days. By way of comparison, the human mesenchymal stem cells were cultured under the same conditions in a commonly used animal cell culture dish (available from Corning Co., Ltd.).

Cell separatability was evaluated by separating the human mesenchymal stem cells on each culture section 102 by a water flow generated in the medium after 5-day incubation. The water flow was generated by ejecting the medium used for the culture from a 200 μl pipette tip attached to a 250 μl pipette (EDP plus EP-250) at an angle of 70° to the bottom surface from a spot close to each culture section 102.

The medium was ejected once and the condition of separation of the cells on each culture section 102 was observed under a microscope, obtaining the results shown in Table 1. In any of the culture sections 102 formed according to the present invention, betterment of separatability of the human mesenchymal stem cells was confirmed in comparison to the animal cell culture dish used for comparison. It was also found that separatability of the human mesenchymal stem cells from the cell culture vessel 100 depended on the diameter R of the projections 101 and was maximized when the diameter was large (R=2 μm). This indicates that adhesiveness of the human mesenchymal stem cells, which are the adhesive cells, is lessened on the projections 101, which attests to the excellent cell separating characteristics of the projections 101. Also, this effect was observed over the entirety of any of the culture sections 102, from which it could be assumed that there substantially existed no human mesenchymal stem cells adhering to the culture sections 102 without receiving the effect of the projections 101.

TABLE 1

| Amount ejected (μl) | Ejection rate (μl/sec) | Example A R = 180 nm | Example B R = 240 nm | Example C R = 500 nm | Example D R = 2 μm | Comparative Example Animal cell culture dish |
|---|---|---|---|---|---|---|
| 50 | 56 | − | − | − | − | − |
|  | 112 | − | ± | ± | + | − |
|  | 192 | + | + | + | + | − |
| 100 | 56 | − | − | − | − | − |
|  | 112 | ± | ± | + | ++ | − |
|  | 192 | ++ | ++ | ++ | ++ | − |
| 200 | 56 | − | − | − | − | − |
|  | 112 | ± | + | + | ++ | − |
|  | 192 | ++ | ++ | ++ | +++ | − |

+++: Could be separated very well.
++: Could be separated well.
+: Could be separated.
±: Could be separated to a limited degree.
−: Could not be separated at all.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A cell culture vessel comprising a culture section provided with a plurality of projections having an equivalent diameter smaller than the cells to be cultured and the culture section side walls enclosing the culture section, wherein the projections having an equivalent diameter smaller than the cells to be cultured are formed over the whole span of the culture section, and the distance between an arbitrary point on the culture section/side wall boundary line and the nearest projection is smaller than the diameter of the cells to be cultured.

2. A cell culture vessel comprising a culture section(s) provided with a plurality of projections having an equivalent diameter smaller than the cells to be cultured and the culture section side walls enclosing the culture section, said vessel also having a buffer section formed between the culture section and its enclosing side walls, said buffer section being located at a lower position than the culture section, wherein the projections having an equivalent diameter smaller than the cells to be cultured are provided over the entirety of the culture section, and the distance between an arbitrary point at an edge of the culture section on the buffer section side and the nearest projection is smaller than the diameter of the cells to be cultured.

3. A cell culture vessel according to claim 1 wherein the culture section is divided into two or more portions by the culture section side walls.

4. A cell culture vessel according to claim 1 wherein the culture section including the projections on its surface and the culture section side walls are made of a same material and formed integral with each other.

5. A cell culture vessel according to claim 1 wherein the culture section and the projections on its surface are made of a same material, and at least part of the culture section side walls is made of a material different from that of the culture section.

6. A cell culture vessel according to claim 1 wherein the culture section and the projections on its surface are made of a same material, and at least part of the culture section side walls are detachable from the culture section.

7. A cell culture vessel according to claim 1 wherein the projections having an equivalent diameter smaller than the cells to be cultured are formed on the culture section side walls.

8. A cell culture vessel according to claim 1 wherein the cells are harder to adhere to the culture section side walls than to the culture section because of formation of a surface structure on the side walls or surface modification which makes the cells less liable to adhere to the side walls.

9. A cell culture vessel according to claim 1 wherein the interval of the projections is smaller than the diameter of the cells to be cultured.

10. A cell culture vessel according to claim 1 wherein the surface projections are 10 nm to 10 μm in equivalent diameter and 10 nm to 1 mm in height.

11. A cell culture vessel according to claim 1 wherein the height of the culture section side walls from the culture section is 0.05 mm to 100 mm, and the angle of inclination to the culture section is 45° or greater.

12. A cell culture vessel according to claim 1 which has a region where the thickness of the vessel is 0.5 mm or greater.

13. A cell culture vessel according to claim 1 wherein the entirety or part of the vessel has been subjected to at least one of the following treatments: hydrophilicity treatment, hydrophobicity treatment, formation of a metallic layer and coating with an organic material.

14. A cell culture vessel according to claim 1 wherein at least one of the following treatments: hydrophilicity treatment, hydrophobicity treatment, formation of a metallic layer and coating with an organic material, has been conducted selectively on a specific region of the vessel.

15. A cell culture vessel according to claim 1 wherein at least one of the following treatments: hydrophilicity treatment, hydrophobicity treatment, formation of a metallic layer and coating with an organic material, has been conducted selectively on the individual projections in the vessel.

16. A cell culture vessel according to claim 1 wherein a hydrophilicity treatment, a hydrophobicity treatment, formation of a metallic layer or coating with an organic material has been conducted on the top ends alone of the projections in the vessel.

17. A cell culture vessel comprising a culture section provided with a plurality of projections having an equivalent diameter smaller than the cells to be cultured and the culture section side walls enclosing the culture section, said culture section being divided into two or more portions by the side walls, wherein the height of the side walls from the culture section is 0.05 to 100 mm, and the thickness of at least part of the vessel is 0.5 mm or greater.

18. A cell culture vessel comprising a culture section provided with a plurality of projections having an equivalent diameter smaller than the cells to be cultured, the culture section side walls enclosing the culture section, and a buffer section disposed between the culture section and its side walls at a position lower than the culture section, wherein said culture section is divided into two or more portions by the side walls, and the width of the buffer section is greater than the diameter of the cells to be cultured.

19. A cell culture vessel according to claim 17 wherein a line of notches or cutouts along which to cut the vessel are provided at a part of the culture section side walls.

20. A cell culture vessel according to claim 17 wherein the divided regions of the culture section differ from each other in at least one of surface treatment on the projections formed on the culture section, height of the projections, diameter of the top ends thereof, equivalent diameter of the projections, their interval and their arrangement.

* * * * *